United States Patent
Ghosh et al.

(10) Patent No.: US 9,550,178 B2
(45) Date of Patent: Jan. 24, 2017

(54) STABLE SILICOALUMINOPHOSPHATE CATALYSTS FOR CONVERSION OF ALKYL HALIDES TO OLEFINS

(71) Applicant: SABIC Global Technologies B.V., Bergen op Zoom (NL)

(72) Inventors: Ashim Kumar Ghosh, Houston, TX (US); Alla Khanmamedova, Sugar Land, TX (US); Mike Mier, Waller, TX (US); Jonathan Banke, Houston, TX (US)

(73) Assignee: SABIC Global Technologies B.V., Amsterdam (NL)

(*) Notice: Subject to any disclaimer, the term of this patent is extended or adjusted under 35 U.S.C. 154(b) by 0 days.

(21) Appl. No.: 14/907,598

(22) PCT Filed: Jul. 28, 2015

(86) PCT No.: PCT/US2015/042478
§ 371 (c)(1),
(2) Date: Jan. 26, 2016

(87) PCT Pub. No.: WO2016/022340
PCT Pub. Date: Feb. 11, 2016

(65) Prior Publication Data
US 2016/0271597 A1   Sep. 22, 2016

Related U.S. Application Data

(60) Provisional application No. 62/033,377, filed on Aug. 5, 2014.

(51) Int. Cl.
| | | |
|---|---|---|
| *C07C 1/26* | (2006.01) | |
| *B01J 29/85* | (2006.01) | |
| *B01J 7/00* | (2006.01) | |
| *B01J 35/10* | (2006.01) | |
| *C01B 39/54* | (2006.01) | |

(52) U.S. Cl.
CPC ........ *B01J 29/85* (2013.01); *B01J 7/00* (2013.01); *B01J 35/1061* (2013.01); *C01B 39/54* (2013.01); *C07C 1/26* (2013.01); *C07C 2529/85* (2013.01); *Y02P 20/584* (2015.11); *Y02P 30/42* (2015.11)

(58) Field of Classification Search
CPC ............... C07C 1/20; C07C 1/22; C07C 1/26; B01J 29/85; B01J 35/1061; B01J 7/00
USPC .............. 585/638, 641, 642, 639, 640
See application file for complete search history.

(56) References Cited

U.S. PATENT DOCUMENTS

| | | | |
|---|---|---|---|
| 4,677,242 A | 6/1987 | Kaiser | 585/638 |
| 6,046,371 A | 4/2000 | Wu et al. | 585/638 |
| 6,137,022 A | 10/2000 | Kuechler et al. | 585/638 |
| 8,603,431 B2 | 12/2013 | Ferrini et al. | 423/700 |
| 2008/0188701 A1 | 8/2008 | Qi et al. | 585/641 |

FOREIGN PATENT DOCUMENTS

| | | |
|---|---|---|
| CN | 101525141 | 2/2012 |
| CN | 102557073 | 7/2012 |
| WO | WO 2010/011423 | 10/2010 |

OTHER PUBLICATIONS

Svelle et al. Journal of Catalysis 241 (2006) 243-254.*
Dai et al., *ACS Catal.* 1(4):292-299, 2011.
International Search Report and Written Opinion for PCT/US2015/042478, mailed Nov. 3, 2015.
Marchi et al., *Applied Catalysis* 71:139-152, 1991.

* cited by examiner

*Primary Examiner* — Sharon Pregler
(74) *Attorney, Agent, or Firm* — Norton Rose Fulbright US LLP (57) ABSTRACT

Disclosed is a method for converting an alkyl halide to an olefin. The method includes contacting a silicoaluminophosphate (SAPO) catalyst with a feed that includes an alkyl halide under reaction conditions sufficient to produce an olefin hydrocarbon product that includes $C_2$ to $C_4$ olefins. The SAPO catalyst has bimodal acidity designated as weak acid sites and strong acid sites. The weak acid concentration is less than 0.55 mmol/g-cat and the total acid concentration is less than 1.5 mmol/g-cat.

20 Claims, 7 Drawing Sheets

STABLE SILICOALUMINOPHOSPHATE CATALYSTS FOR CONVERSION OF ALKYL HALIDES TO OLEFINS

CROSS REFERENCE TO RELATED APPLICATIONS

This application is a national phase application under 35 U.S.C. 371 of International Application No. PCT/US2015/042478 filed Jul. 28, 2015, which claims benefit of U.S. Provisional Patent Application No. 62/033,377 titled "STABLE SILICOALUMINOPHOSPHATE CATALYSTS FOR CONVERSION OF ALKYL HALIDES TO OLEFINS" filed Aug. 5, 2014. The entire content of the referenced applications are incorporated herein by reference.

BACKGROUND OF THE INVENTION

A. Field of the Invention

The invention generally concerns the use of small pore size silicoaluminophosphate (SAPO) catalysts to produce light olefins from alkyl halides. In particular, the catalysts have a weak acid concentration of less than 0.55 mmol/g-cat, a total acid concentration of 1.5 mmol/g-cat or less, and exhibit improved stability and catalytic performance over prolong periods of use.

B. Description of Related Art

Descriptions of units, abbreviation, terminology, etc. used throughout the present invention are summarized in Table 1.

Figure 1A:
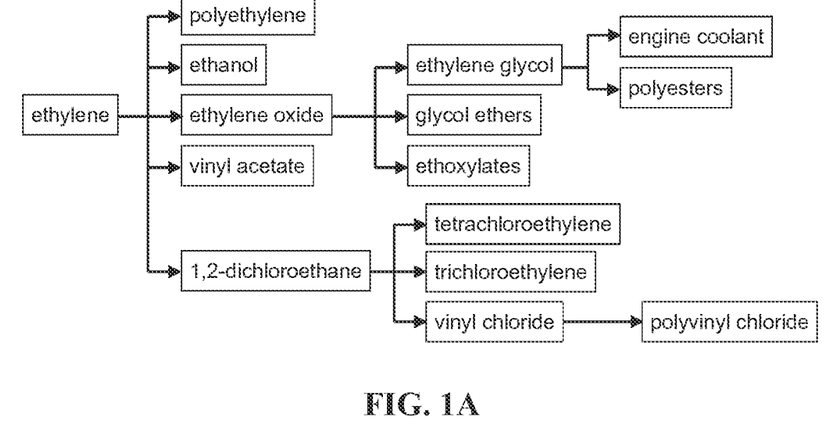
FIGS. 1A and 1B: Illustrations of various chemicals and products that can be produced from ethylene (FIG. 1A) and propylene (FIG. 1B).
Figure 1B:
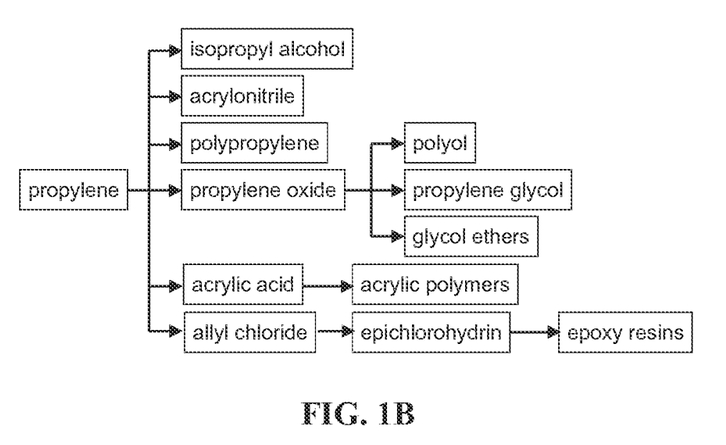

Light olefins such as ethylene and propylene are used by the petrochemical industry to produce a variety of key chemicals that are then used to make numerous downstream products. By way of example, both of these olefins are used to make a multitude of plastic products that are incorporated into many articles and goods of manufacture. FIGS. 1A and 1B provide examples of products generated from ethylene (FIG. 1A) and propylene (FIG. 1B).

Methane activation to higher hydrocarbons, especially to light olefins, has been the subject of great interest over many decades. Recently, the conversion of methane to light olefins via a two-step process that includes conversion of methane to methyl halide, particularly to methyl mono-halide, for example, to methyl chloride followed by conversion of the halide to light olefins has attracted great attention. Zeolite (e.g., ZSM-5) or zeolite type catalysts (e.g., SAPO-34) have been tried for methyl chloride (or other methyl halide) conversion. However, the selectivity to a desired olefin (e.g., propylene) and the rapid catalyst deactivation for the halide reaction remain the major challenges for commercial success.

One of the most commonly used catalysts in the petrochemical industry is ZSM-5 zeolite. It is a medium pore zeolite with pore size about 5.5 Å and is shown to convert methyl halide, particularly methyl chloride or methyl bromide, to $C_2$-$C_4$ olefins and aromatics under methyl halide reaction conditions. Whereas, molecular sieve SAPO-34, an isostructure of chabazite zeolite, having small pore opening (3.8 Å) is shown to convert methyl halide to ethylene and propylene and small amounts of $C_4$ olefins. However, both catalysts are shown to deactivate rapidly during methyl halide conversion due to carbon deposition on the catalysts.

While the SAPO-34 catalyst has good selectivity for both ethylene and propylene, a major problem with the SAPO-34 catalyst is its lack of stable catalytic performance over prolonged periods of use for the alkyl halide conversion. Notably, the currently available SAPO-34 catalysts show methyl chloride conversion rates of less than 20% after being used for 20 h. Such deactivation of these catalysts require frequent or continuous catalyst regeneration, or frequent catalyst change-out resulting in inefficient plant operation, or use of more catalysts to produce the desired amounts of ethylene and propylene, which in turn increases the manufacturing costs. Still further, the catalytic material has to be re-supplied in shorter time intervals, which oftentimes requires the reaction process to be shut down. This also adds to the inefficiencies of the currently available SAPO-34 catalysts.

TABLE 1

| Abbreviation | Description |
| --- | --- |
| Å | Angstrom |
| Avg. | Average |
| BET SA | BET (Brunauer-Emmett-Teller) surface area |
| ° C. | degree Celsius |
| ° C./min | degree Celsius per minute |
| $cm^3$/min | cubic centimeter per min |
| g | gram |
| $g/cm^3$ | gram per cubic centimeter |
| h | hour |
| $m^2$/g | meter square per gram |
| mol % | mole percent |
| mmol/g-cat | millimole per gram of catalyst |
| $NH_3$-TPD | ammonia temperature programmed desorption |
| % | percent |
| psig | pound per square inch gauge |
| SAR | silica to alumina ratio |
| XRF | X-ray fluorescence |
| WHSV | weight hourly space velocity |
| wt. % | weight percent |

SUMMARY OF THE INVENTION

A discovery has been made that solves the rapid catalyst deactivation problems associated with small pore size molecular sieve catalysts (e.g., silicoaluminophosphate (SAPO)) without compromising their selectivity for ethylene and propylene production. The discovery is premised on reducing the silica content in SAPO catalysts, thereby reducing the acid concentration, particularly the weak acid sites. In particular, the present discovery illustrates that SAPO catalysts having a weak acid concentration of less than 0.55 mmol/g-cat and a total acid concentration of less than 1.5 mmol/g-cat results in improved stability when converting alkyl halides (e.g., methyl halide) to light olefins (e.g., ethylene and propylene). This enhanced stability allows for a more efficient process of making light olefins when compared with the currently available SAPO catalysts. For instance, less catalytic material is needed and the frequency in regenerating spent catalysts is reduced without compromising the selectivity of light olefin production.

In one aspect of the present invention there is disclosed a catalyst capable of producing an olefin from an alkyl halide. The catalyst can includes silicoaluminophosphate (SAPO) framework structure containing a small pore opening. In particular, SAPO can be a SAPO-34 having framework structure with pore opening of 3.8 Å. The catalyst exhibits bimodal acidity and has two major broad peaks as characterized by ammonia temperature programmed desorption ($NH_3$-TPD) technique, one with peak maximum between 150 and 200° C., and the other with peak maximum between 250 and 450° C. The lower temperature peak is attributed to weak acid sites while the higher temperature peak is attributed to strong acid sites. The particular SAPO-34 can be modified during synthesis or post synthesis modification to possess weak acid concentration of less than 0.55 mmol/g- cat and total acid concentration of less than 1.5 mmol/g-cat. In particular instances, the SAPO-34 can contain less than about 4.0 wt. % Si and the total acid concentration less than 1.3 mmol/g-cat, or the SAPO-34 catalyst contain about 4.0 to 1.0 wt. % Si. In more particular instances the catalyst can contain total acid concentration ranging from 1.3 mmol/g-cat to 0.5 mmol/g-cat, and weak acid concentration of less than 0.55 mmol/g-cat. In one preferred instance, the SAPO-34 catalyst can have less than about 3.5 wt. % Si and weak acid less than about 0.45 mmol/g-cat and a total acid concentration about 1.2 mmol/g-cat. In some particular instances, the catalysts can have about 1.4 wt. % Si and weak acid concentration of about 0.2 mmol/g-cat. In other instances, the catalysts can have about 3.5 wt. % Si and weak acid concentration of about 0.45 mmol/g-cat. In some preferred aspects, the SAPO catalyst can be SAPO-34. In other preferred aspects, the SAPO-34 catalysts can have an average particle size of about 0.2 to 1.0 μm or 0.20 to 0.6 μm. The SAPO catalysts of the present invention can have an average pore opening of 3.5 to 4.5 angstroms. In some aspects, the SAPO catalysts of the present invention can have Si content of less than 4.0 wt. %, or less than 3.5 to 0.5 wt. %, or about 2.0 to 1.0 wt. %. The SAPO catalysts can have phosphorus content of 17 to 20 wt. %, and aluminum content of 22 to 24 wt. %. In some instances, the SAPO catalysts can have a Si/(Al+P) ratio of less than 0.17 or less than 0.17 to greater than 0.01.

In certain aspects, the SAPO catalysts are capable of converting at least 25% or at least 30% of the alkyl halide after 20 hours of use at a temperature of 300° C. to 375° C., and WHSV of the halide feed of greater than 0.5 h$^{-1}$ or of between 0.5 and 1.5 h$^{-1}$. In some particular instances, the catalyst is capable of converting 25 to 50% of the alkyl halide after 20 hours of use at a temperature of 300° C. to 375° C. The catalysts can have a selectivity of $C_2$-$C_3$ olefins of at least 80% after 20 hours of use at a temperature of 300° C. to 375° C. In certain aspects, the selectivity of ethylene can be at least 40%, and the selectivity of propylene can be at least 40% after 20 hours of use at a temperature of 300° C. to 375° C. In preferred aspects, the combined selectivity of ethylene and propylene can be at least 80% at 30% alkyl halide conversion at 300° C. to 375° C. The catalyst deactivation rate as measured by decrease of conversion per unit time (whereby higher number means faster catalyst deactivation) under the reaction conditions can be less than 4% conversion decrease per hour after the reaction induction time. In one preferred instance, the catalyst deactivation rate can be less than 2% conversion decrease per hour.

The alkyl halide comprised within the feed can have the following structure: $C_nH_{(2n+2)-m}X_m$, where n and m are integers, n ranges from 1 to 5, preferably 1 to 3, even more preferably 1, m ranges 1 to 3, preferably 1, X is Br, F, I, or Cl. The feed can include about 10, 15, 20, 40, 50 mol % or more of an alkyl halide such as methyl halide. In particular aspects, the feed can include about 10 to 30 or about 20 mol % of the alkyl halide. Non-limiting examples of methyl halides include methyl chloride, methyl bromide, methyl fluoride, or methyl iodide, or any combination thereof. In particular embodiment, the alkyl halide is methyl chloride or methyl bromide. The method can further include collecting or storing the produced olefin hydrocarbon product along with using the produced olefin hydrocarbon product to produce a petrochemical or a polymer. Additionally, the used and deactivated catalyst can be regenerated (e.g., after 5, 10, 15, 20, 25, or 30 hours of use, the catalyst can be regenerated).

The decrease of alkyl halide conversion can be attributed to carbon deposition on the SAPO catalyst. The carbon deposition causes the blockage of active sites resulting in decrease of conversion. The spent catalyst can be regenerated by burning of the deposited carbon. Such carbon burning can generally be performed by heating the spent catalyst under oxygen, preferably diluted oxygen, often used air, at temperature between 400 to 600° C.

In still another embodiment of the present invention there is disclosed a system for producing olefins. The system can include an inlet for a feed that includes the alkyl halide discussed above and throughout this specification, a reaction zone that is configured to be in fluid communication with the inlet, wherein the reaction zone can include any one of the SAPO catalysts of the present invention that are discussed above and throughout this specification, and an outlet configured to be in fluid communication with the reaction zone to remove an olefin hydrocarbon product from the reaction zone. During use, the reaction zone can further include the alkyl halide feed and the olefin hydrocarbon product (e.g., ethylene, propylene, and/or butylene). The temperature of the reaction zone can be 325 to 375° C. The system can include a collection device that is capable of collecting the olefin hydrocarbon product.

Also disclosed is a method of synthesizing any one of the silicoaluminophosphate (SAPO) catalysts of the present invention. The method can include making a gel containing the sources of Si, Al, and P, and a structure directing agent, and heating the gel mixture at a temperature of 200° C. to 225° C. under conditions to produce the SAPO catalyst. A non-limiting example of a silica containing material includes colloidal silica. A non-limiting example of an aluminum containing material includes aluminum isopropoxide. A non-limiting example of a phosphorus containing material includes phosphoric acid. A non-limiting example of a structure directing agent includes tetramethylammonium hydroxide, which can be added to the mixture prior to heating the mixture. The synthesized SAPO catalyst can be further separated from the mixture and washed with water followed by drying around 100° C. The process can further include calcining the produced SAPO catalyst at a temperature of 400 to 600° C. for more than 0.5 h, preferably more than 2 h and less than 20 h.

In the context of the present invention, embodiments 1-45 are described. Embodiment 1 is a method for converting an alkyl halide to an olefin. The method includes contacting a silicoaluminophosphate (SAPO) catalyst with a feed that includes an alkyl halide under reaction conditions sufficient to produce an olefin hydrocarbon product that includes $C_2$ to $C_4$ olefins, wherein the SAPO catalyst has bimodal acidity designated as weak acid sites and strong acid sites, wherein the weak acid concentration is less than 0.55 mmol/g-cat and the total acid concentration is less than 1.5 mmol/g-cat. Embodiment 2 is the method of embodiment 1, wherein the SAPO catalyst has a weak acid concentration of 0.1 to 0.3 mmol/g-cat and a total acid concentration of less than 0.7 mmol/g-cat. Embodiment 3 is the method of embodiment 2, wherein the SAPO catalyst has a weak acid concentration of 0.15 to 0.25 mmol/g-cat and a total acid concentration of 0.5 to 0.7 mmol/g-cat. Embodiment 4 is the method of embodiment 3, wherein the SAPO catalyst has 1 to 2 wt. % of Si. Embodiment 5 is the method of embodiment 1, wherein the SAPO catalyst has a weak acid concentration of 0.3 to 0.5 mmol/g-cat and a total acid concentration of 1.3 mmol/g-cat or less. Embodiment 6 is the method of embodiment 5, wherein the SAPO catalyst has a weak acid concentration of 0.35 to 0.45 mmol/g-cat and a total acid concentration of 1 to 1.25 mmol/g-cat. Embodiment 7 is the method of embodiment 6, wherein the SAPO catalyst has 3 to 4 wt. % of Si. Embodiment 8 is the method of embodiment 1, wherein the SAPO catalyst has a weak acid concentration of 0.50 mmol/g-cat or less and a total acid concentration of 1.3 mmol/g-cat or less. Embodiment 9 is the method of any one of embodiments 1 or 8, wherein the SAPO catalyst has 4 wt. % or less of Si or 1 to 4 wt. % of Si. Embodiment 10 is the method of any one of embodiments 1 to 9, wherein the SAPO catalyst is SAPO-34. Embodiment 11 is the method of any one of embodiments 1 to 10, wherein the SAPO catalyst has an average particle size of 0.1 μm to 1 μm, preferably from 0.2 μm to 0.6 μm, and most preferably of about 0.4 μm. Embodiment 12 is the method of any one of embodiments 1 to 11, wherein the SAPO catalyst has an average pore opening of 3.5 to 4.5 angstroms. Embodiment 13 is the method of any one of embodiments 1 to 12, wherein the SAPO catalyst has a P content of 17 to 20 wt. % and an Al content of 22 to 24 wt. %. Embodiment 14 is the method of embodiment 13, wherein the SAPO catalyst has an Si/(Al+P) ratio of less than 0.17 or 0.01 to less than 0.17. Embodiment 15 is the method of any one of embodiments 1 to 14, wherein the SAPO catalyst deactivation rate is less than 5% or from 2% to 5% or from 2% to 3% alkyl halide conversion decrease per hour. Embodiment 16 is the method of any one of embodiments 1 to 15, wherein the alkyl halide conversion is at least 25% or 25% to 50% at 20 hours of use at a temperature of 300° C. to 375° C. and a WHSV of the halide feed of 0.5 and 1.5 $h^{-1}$. Embodiment 17 is the method of embodiment 16, wherein the combined selectivity of ethylene and propylene is at least 80%. Embodiment 18 is the method of any one of embodiments 1 to 17, wherein the alkyl halide is a methyl halide. Embodiment 19 is the method of embodiment 18, wherein the methyl halide is methyl chloride, methyl bromide, methyl fluoride, or methyl iodide, or any combination thereof. Embodiment 20 is the method of embodiment 19, wherein the methyl halide is methyl chloride. Embodiment 21 is the method of any one of embodiments 1 to 20, wherein the feed includes about 10 mol % or more of the alkyl halide. Embodiment 22 is the method of any one of embodiments 1 to 21, further including collecting or storing the produced olefin hydrocarbon product. Embodiment 23 is the method of any one of embodiments 1 to 22, further including using the produced olefin hydrocarbon product to produce a petrochemical or a polymer. Embodiment 24 is the method of any one of embodiments 1 to 23, further including regenerating the used catalyst after 20, 25, or 30 hours of use. Embodiment 25 is the method of any one of embodiments 1 to 24, wherein the SAPO catalyst is not a substituted SAPO-34 catalyst, preferably not a Ti-SAPO-34 catalyst.

Embodiment 26 is a silicoaluminophosphate (SAPO) catalyst capable of converting a feed that includes an alkyl halide to an olefin hydrocarbon product, the SAPO catalyst having bimodal acidity designated as weak acid sites and strong acid sites, wherein the weak acid concentration is less than 0.55 mmol/g-cat and the total acid concentration is less than 1.5 mmol/g-cat. Embodiment 27 is the SAPO catalyst of embodiment 26, having a weak acid concentration of 0.1 to 0.3 mmol/g-cat and a total a total acid concentration of less than 0.7 mmol/g-cat. Embodiment 28 is the SAPO catalyst of embodiment 27, having a weak acid concentration of 0.15 to 0.25 mmol/g-cat and a total acid concentration of 0.5 to 0.7 mmol/g-cat. Embodiment 29 is the SAPO catalyst of embodiment 28, having a 1 to 2 wt. % of Si. Embodiment 30 is the SAPO catalyst of embodiment 26, having a weak acid concentration of 0.3 to 0.5 mmol/g-cat and a total a total acid concentration of 1.3 mmol/g-cat or less. Embodiment 31 is the SAPO catalyst of embodiment 30, having a weak acid concentration of 0.35 to 0.45 mmol/g-cat and a total acid concentration of 1 to 1.25 mmol/g-cat. Embodiment 32 is the SAPO catalyst of embodiment 31, having a 3 to 4 wt. % of Si. Embodiment 33 is the SAPO catalyst of embodiment 26, having a weak acid concentration of 0.50 mmol/g-cat or less and a total acid concentration of 1.3 mmol/g-cat or less. Embodiment 34 is the SAPO catalyst of any one of embodiments 26 or 33, having 4 wt. % or less of Si or 1 to 4 wt. % of Si. Embodiment 35 is the SAPO catalyst of any one of embodiments 26 to 34, wherein the SAPO catalyst is SAPO-34. Embodiment 36 is the SAPO catalyst of any one of embodiments 26 to 35, having an average particle size of 0.6 μm or 0.20 μm to 0.6 μm. Embodiment 37 is the SAPO catalyst of any one of embodiments 26 to 36, having an average pore opening of 3.5 to 4.5 angstroms. Embodiment 38 is the SAPO catalyst of any one of embodiments 26 to 37, having a P content of 17 to 20 wt. % and an Al content of 22 to 24 wt. %. Embodiment 39 is the SAPO catalyst of embodiment 38, having an Si/(Al+P) ratio of less than 0.17 or 0.01 to less than 0.17. Embodiment 40 is the SAPO catalyst of any one of embodiments 26 to 39, having been calcined at a temperature of 400 to 600° C. Embodiment 41 is the SAPO catalyst of any one of embodiments 26 to 40, wherein the SAPO catalyst is not a substituted SAPO-34 catalyst, preferably not a Ti-SAPO-34 catalyst.

Embodiment 42 is a system for producing olefins. The system includes an inlet for a feed including an alkyl halide; a reaction zone that is configured to be in fluid communication with the inlet, wherein the reaction zone includes any one of the silicoaluminophosphate (SAPO) catalysts of embodiments 26 to 41; and an outlet configured to be in fluid communication with the reaction zone to remove an olefin hydrocarbon product from the reaction zone. Embodiment 42 is the system of embodiment 42, wherein the reaction zone further includes the feed and the olefin hydrocarbon product. Embodiment 44 is the system of embodiment 43, wherein the olefin hydrocarbon product includes ethylene and propylene. Embodiment 45 is the system of any one of embodiments 42 to 44, further includes a collection device that is capable of collecting the olefin hydrocarbon product.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The use of the word "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The catalysts of the present invention can "comprise," "consist essentially of," or "consist of" particular ingredients, components, compositions, etc. disclosed throughout the specification. With respect to the transitional phase "consisting essentially of," in one non-limiting aspect, basic and novel characteristics of the catalysts of the present invention are their ability to selectivity produce light olefins, and in particular, ethylene and propylene, in high amounts, while also remaining stable/activated after prolonged periods of use (e.g., 20 hours).

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

DETAILED DESCRIPTION OF THE INVENTION

The currently available SAPO catalysts, particularly SAPO-34 catalysts, show high activity for alkyl halide conversion with selectivity to light olefins (e.g., ethylene and propylene). These types of catalysts, however, tend to deactivate rapidly during the initial periods of the reaction reaching an unacceptable level of alkyl halide conversion within hours. This rapid deactivation leads to a number of processing and cost inefficiencies.

A discovery has been made that results in SAPO catalysts having improved stability showing slower catalyst deactivation for converting alkyl halides to light olefins. The stability is obtained by using SAPO catalysts that have weak acid concentrations of less than 0.55 mmol/g-cat and total acid concentrations of less than 1.5 mmol/g-cat. This improved stability results in a more efficient and continuous production of light olefins from alkyl halides without having to continuously regenerate spent catalysts or constantly provide additional catalysts to the reaction process.

These and other non-limiting aspects of the present invention are discussed in further detail in the following sections.

A. SAPO Catalysts

The SAPO catalysts of the present invention are designed such that they exhibit bimodal acidity and have two major broad peaks as characterized by ammonia temperature programmed desorption ($NH_3$-TPD) technique, one with peak maximum between 150 and 200° C., and the other with peak maximum between 250 and 450° C. The lower temperature peak is attributed to weak acid sites while the higher temperature peak is attributed to strong acid sites. In a preferred aspect of the present invention, SAPO catalysts can have weak acid sites or acid concentration of less than 0.55 mmol/g-cat and total acid concentration of about 1.5 mmol/g-cat or less.

The SAPO catalysts have an open microporous structure with regularly sized channels, pores or "cages." These materials are sometimes referred to as "molecular sieves" in that they have the ability to sort molecules or ions based primarily on the size of the molecules or ions. SAPO materials are both microporous and crystalline and have a three-dimensional crystal framework of $PO_4^+$, $AlO_4^-$ and $SiO_4$ tetrahedra. The empirical chemical composition on an anhydrous basis is:

where, R represents at least one organic templating agent present in the intracrystalline pore system; m represents the moles of R present per mole of $(Si_xAl_yP_z)O_2$ and has a value from zero to 0.3; and x, y, and z represent the mole fractions of silicon, aluminum, and phosphorus, respectively, present as tetrahedral oxides.

Non-limiting examples of making SAPO catalysts of the present invention are provided in the Examples section. Additionally, existing SAPO materials can be modified to have the desired weak acid concentration (i.e., 0.55 mmol/g-cat or less) and total acid concentration (i.e., 1.5 mmol/g-cat or less). For instance, existing SAPO materials can be modified by reducing the total amount of Si present in the material to less than 7 wt. % or preferably to 1 to 4 wt. %. Additionally, the SAPO materials can be treated (e.g., with P) to reduce the acidity of the SAPO material. In either event, techniques standard to those of skill in the art can be used to make such modifications.

Non-limiting examples of SAPO materials that can be used to make the catalysts of the present invention include SAPO materials that contain eight member ring openings and a pore size from about 3.5 Å to about 4.5 Å (e.g., SAPO-17, SAPO-18, SAPO-34, SAPO-35, SAPO-42, and SAPO-44). The relationship between the SAPO numbers and their structures is mentioned, for example, in Encyclopedia of Inorganic Chemistry, Vol. 8, 4369 (1994). For instance, the IUPAC codes corresponding to SAPO-17, 18, 34, 35, 42, and 44 are ERI, AEI, CHA, LEV, LTA, and CHA, respectively. A preferred SAPO material is SAPO-34. SAPO-34 has the same framework structure of chabazite zeolite. SAPO-34 and processes of making SAPO-34 are disclosed in U.S. Pat. No. 4,440,871, which is incorporated by reference.

In some embodiments, the SAPO framework can be modified to contain one or more elements from Groups 2A, 3A, IVB, VIB, VIIB, VIII, 1B of the Periodic Table by partly substituting aluminum and/or phosphorus in the framework structure with the appropriate element to obtain substituted-SAPO structures. Framework modified SAPO structures may be represented by the formula: Z-SAPO, where Z is the element that is substituted in the framework and the hyphen designates that the element is in the framework. Examples of elements from Group 2A include beryllium (Be) and compounds thereof. Examples of elements from Group 3A include boron and compounds thereof. Examples of elements from Group IB include copper and compounds thereof. Examples of elements from Group IVB include titanium, zirconium, hafnium, and compounds thereof. Examples of elements from Group VIB include chromium, molybdenum, tungsten and compounds thereof. Examples of elements from Group VIIB include manganese and compounds thereon. Examples of elements from Group VIII include cobalt, nickel, iron, and compounds thereof.

B. Alkyl Halide Feed

The alkyl halide feed includes one or more alkyl halides. The alkyl halide feed may contain alkyl mono halides, alkyl dihalides, alkyl trihalides, preferably alkyl mono halide with less than 10% of other halides relative to the total halides. The alkyl halide feed may also contain nitrogen, helium, steam, and so on as inert compounds. The alkyl halide in the feed may have the following structure: $C_nH_{(2n+2)-m}X_m$, where n and m are integers, n ranges from 1 to 5, preferably 1 to 3, even more preferably 1, m ranges 1 to 3, preferably 1, X is Br, F, I, or Cl. Non-limiting examples of methyl halides include methyl chloride, methyl bromide, methyl fluoride, or methyl iodide, or any combination thereof. In particular aspects, the feed may include about 10, 15, 20, 40, 50 mol % or more of the alkyl halide. In particular embodiments, the feed contains up to 20% of the feed includes an alkyl halide. In preferred aspects, the alkyl halide is methyl chloride. In particular embodiment, the alkyl halide is methyl chloride or methyl bromide.

The production of alkyl halide particularly of methyl chloride ($CH_3Cl$, See Equation 1 below) is commercially produced by thermal chlorination of methane at 400° C. to 450° C. and at a raised pressure. Catalytic oxychlorination of methane to methyl chloride is also known. In addition, methyl chloride is industrially made by reaction of methanol and HCl at 180° C. to 200° C. using a catalyst. Alternatively, methyl halides are commercially available from a wide range of sources (e.g., Praxair, Danbury, Conn.; Sigma-Aldrich Co. LLC, St. Louis, Mo.; BOC Sciences USA, Shirley, N.Y.). In preferred aspects, methyl chloride and methyl bromide can be used alone or in combination.

C. Olefin Production

The SAPO catalysts of the present invention help to catalyze the conversion of alkyl halides to light olefins such as ethylene and propylene. The following non-limiting two-step process is an example of conversion of methane to methyl halide and conversion of methyl halide to ethylene and propylene. The second step illustrates the reactions that are believed to occur in the context of the present invention.

$$CH_4 + X_2 \xrightarrow{SAPO\ CATALYST} CH_3X + HX \quad \text{(Equation 1)}$$

$$5CH_3X \rightarrow C_2H_4 + C_3H_6 + 5HX \quad \text{(Equation 2)}$$

where X is Br, F, I, or Cl. Besides the light olefins the reaction may produce byproducts such as methane and $C_4$-$C_5$ olefins.

Conditions sufficient for olefin production (e.g., ethylene and propylene as shown in Equation 2) include temperature, time, alkyl halide concentration, space velocity, and pressure. The temperature range for olefin production may range from about 300° C. to 500° C., preferably ranging 350° C. to 450° C. In more preferred aspects, the temperature range is from 325° C. to 375° C. A weight hour space velocity (WHSV) of higher than 0.5 $h^{-1}$ can be used, preferably between 0.5 and 10 $h^{-1}$, more preferably between 0.7 and 3.0 $h^{-1}$, even more preferably between 0.7 and 1.1 $h^{-1}$. The conversion of alkyl halide is carried out at a pressure less than 200 psig preferably less than 100 psig, more preferably less than 50 psig, even more preferably less than 20 psig. The conditions for olefin production may be varied based on the type or size of reactor.

The reaction can be carried out for prolonged periods of time without changing or re-supplying new catalyst or catalyst regeneration. This is due to the stability or slower deactivation of the catalysts of the present invention. Therefore, the reaction can be performed for a period until the level of alkyl halide conversion reaches to a preset level (e.g., 30%). In preferred aspects, the reaction is continuously run for 20 h or 20 h to 40 h or longer without having to stop the reaction to resupply new catalyst or catalyst regeneration. The method can further include collecting or storing the produced olefin hydrocarbon product along with using the produced olefin hydrocarbon product to produce a petrochemical or a polymer.

D. Olefin Selectivity

Catalytic activity as measured by alkyl halide conversion can be expressed as the % moles of the alkyl halide converted with respect to the moles of alkyl halide fed. In some aspects, the catalysts show a combined selectivity of ethylene and propylene of at least 80%, or between 85-90% after 20 hours of use at reaction conditions which include temperature of 325 to 375° C., WHSV (of alkyl halide) of 0.7 to 1.1 $h^{-1}$, reactor pressure of less than 20 psig, preferably, less than 5 psig, or more preferably of 1 to 3 psig. The combined selectivity of ethylene, propylene and butylene of SAPO catalysts of the present invention can be at least 80%, or about 85% and 90% or more after 20 hours of use at a temperature of 325 to 375° C. As an example, methyl chloride ($CH_3Cl$) is used here to define conversion and selectivity of products by the following formulas:

$$\% \ CH_3Cl \ Conversion = \frac{(CH_3Cl)^o - (CH_3Cl)}{(CH_3Cl)^o} \times 100 \quad \text{(Equation 3)}$$

where, $(CH_3Cl)^o$ and $(CH_3Cl)$ are moles of methyl chloride in the feed and reaction product, respectively.

Selectivity for ethylene may be expressed as:

$$C_2H_4 \ Sel\ (C\text{-mol }\%) = \frac{2(C_2H_4)}{(CH_4) + 2(C_2H_4) + 2(C_2H_6) + 3(C_3H_6) + 3(C_3H_8) + 4(C_4H_8) + 4(C_4H_{10}) + \ldots} \times 100 \quad \text{(Equation 4)}$$

where, the numerator is the carbon adjusted molar quantity of ethylene and the denominator is the sum of all the carbon adjusted moles of all hydrocarbons in the product stream.

Selectivity for propylene may be expressed as:

$$C_3H_6 \ Sel\ (C\text{-mol }\%) = \frac{3(C_3H_6)}{(CH_4) + 2(C_2H_4) + 2(C_2H_6) + 3(C_3H_6) + 3(C_3H_8) + 4(C_4H_8) + 4(C_4H_{10}) + \ldots} \times 100 \quad \text{(Equation 5)}$$

where, the numerator is the carbon adjusted molar quantity of propylene and the denominator is the sum of all the carbon adjusted moles of all hydrocarbons in the product stream.

Selectivity for butylene may be expressed as:

$$C_4H_8 \ Sel\ (C\text{-mol }\%) = \frac{4(C_4H_8)}{(CH_4) + 2(C_2H_4) + 2(C_2H_6) + 3(C_3H_6) + 3(C_3H_8) + 4(C_4H_8) + 4(C_4H_{10}) + \ldots} \times 100 \quad \text{(Equation 6)}$$

where, the numerator is the carbon adjusted molar quantity of butylene and the denominator is the sum of all the carbon adjusted moles of all hydrocarbons in the product stream.

Selectivity for aromatic compounds may be expressed as:

$$\text{Aromatics Sel (C-mol \%)} = \frac{6(C_6H_6) + 7(C_7H_8) + 8(C_8H_{10})}{(CH_4) + 2(C_2H_4) + 2(C_2H_6) + 3(C_3H_6) + 3(C_3H_8) + 4(C_4H_8) + 4(C_4H_{10}) + \ldots} \times 100 \quad \text{(Equation 7)}$$

where, the numerator is the carbon adjusted molar quantity of aromatics (benzene, toluene and xylene) and the denominator is the sum of all the carbon adjusted moles of all hydrocarbons in the product stream.

E. Olefin Production System

Figure 2:
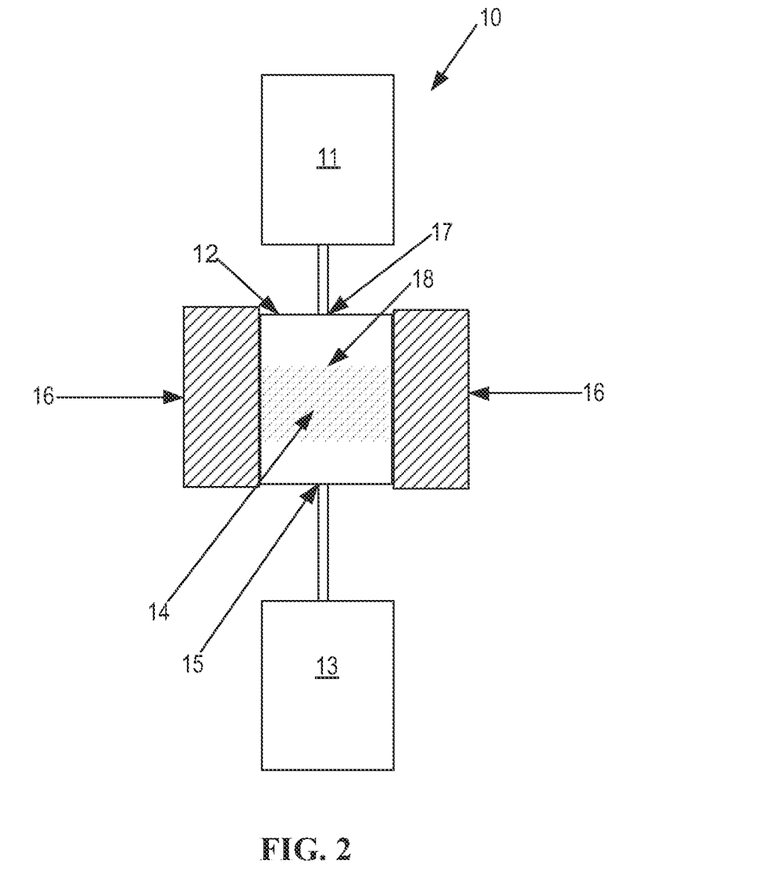
FIG. 2: Illustration of a system for producing olefins from alkyl halides.

Referring to FIG. 2, a system 10 is illustrated, which can be used to convert alkyl halides to olefin hydrocarbon products with the SAPO catalysts of the present invention. The system 10 can include an alkyl halide source 11, a reactor 12, and a collection device 13. The alkyl halide source 11 can be configured to be in fluid communication with the reactor 12 via an inlet 17 on the reactor. As explained above, the alkyl halide source can be configured such that it regulates the amount of alkyl halide feed entering the reactor 12. The reactor 12 can include a reaction zone 18 having the SAPO catalyst 14 of the present invention. Non-limiting examples of reactors that can be used include fixed-bed reactors, fluidized bed reactors, bubbling bed reactors, slurry reactors, rotating kiln reactors, or any combinations thereof when two or more reactors are used. In preferred aspects, a fixed bed reactor can be used. The amount of the catalyst 14 used can be modified as desired to achieve a given amount of product produced by the system 10. A non-limiting example of a reactor 12 that can be used is a fixed-bed reactor (e.g., a fixed-bed tubular stainless steel reactor which can be operated at atmospheric pressure). The reactor 12 can include an outlet 15 for products produced in the reaction zone 18. The products produced can include ethylene and propylene. The collection device 13 can be in fluid communication with the reactor 12 via the outlet 15. Both the inlet 17 and the outlet 15 can be open and closed as desired. The collection device 13 can be configured to store, further process, or transfer desired reaction products (e.g., ethylene or propylene) for other uses. By way of example only, FIG. 1 provides non-limiting uses of ethylene (FIG. 1A) and propylene (FIG. 1B) produced from the catalysts and processes of the present invention. Still further, the system 10 can also include a heating source 16. The heating source 16 can be configured to heat the reaction zone 18 to a temperature sufficient (e.g., 325° C. to 375° C.) to convert the alkyl halides in the alkyl halide feed to olefin hydrocarbon products. A non-limiting example of a heating source 16 can be a temperature controlled furnace. Additionally, any unreacted alkyl halide can be recycled and included in the alkyl halide feed to further maximize the overall conversion of alkyl halide to olefin products. Further, certain products or byproducts such as butylene, $C_{5+}$ olefins and $C_{2+}$ alkanes can be separated and used in other processes to produce commercially valuable chemicals (e.g., ethylene, propylene). This increases the efficiency and commercial value of the alkyl halide conversion process of the present invention.

Conditions sufficient for light olefin production (e.g., ethylene and propylene as shown in Equation 2) include temperature, time, alkyl halide concentration, space velocity, and pressure. The temperature range for olefin production may range from about 300° C. to 500° C., preferably ranging 350° C. to 450° C. In more preferred aspects, the temperature range is from 325° C. to 375° C. A weight hourly space velocity (WHSV) of alkyl halide higher than 0.5 $h^{-1}$ can be used, preferably between 0.5 and 10 $h^{-1}$, more preferably between 0.5 and 5 $h^{-1}$, even more preferably between 0.5 to 1.0 $h^{-1}$. The conversion of alkyl halide is carried out at a pressure less than 200 psig preferably less than 100 psig, more preferably less than 50 psig, even more preferably less than 20 psig. The conditions for olefin production may be varied based on the type of the reactor.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results. The materials used in the following examples are described in Table 2, and were used as-described unless specifically stated otherwise.

TABLE 2

| Material | Source |
|---|---|
| SAPO-34 (powder form)[a] | ACS Material |
| Colloidal Silica (Ludox SM-30) | Sigma-Aldrich |
| Aluminum iso-propoxide (Al(O—i-Pr)$_3$) | Sigma-Aldrich |
| Phosphoric acid ($H_3PO_4$ (85 wt % in aqueous)) | Sigma Aldrich |
| Hydrochloric acid (HCl) | Sigma-Aldrich |
| Tetraethylammonium hydroxide (($C_2H_5)_4$N(OH)) | Sigma Aldrich |
| Water (deionized) | SABIC labs |

[a]SAPO-34 obtained from ACS Material, Medford, MA, USA.

Comparative Catalyst

Catalyst A.

A SAPO-34 powder was obtained from a commercial source (ACS Material). The SAPO-34 powder was calcined in air at 550° C. for 2 h and designated as Catalyst A.

Example Catalyst

Catalyst B.

A mixture was prepared by adding 13.65 g aluminum isopropoxide to 18.15 g water in a Teflon liner, stirred at 60° C. in a hot water bath for 2 h. The isopropoxide mixture was cooled to room temperature and a mixture of phosphoric acid and hydrochloric acid (5.49 g $H_3PO_4$ and 1.55 g HCl) was added dropwise while stirring. Silica gel (4.00 g Ludox SM-30) was added to the mixture while stirring and 28.12 g tetraethylammonium hydroxide was slowly added while vigorously stirred. The gel mixture was aged overnight at room temperature without stirring. The gel was heated at 215° C. for 99 h in static autoclave. The formed SAPO material was separated and washed with water, and dried at 90° C. overnight. The material was sieved through 40 mesh screen and calcined in air at 600° C. for 2 h.

Catalyst C.

A mixture was prepared by adding 13.60 g of aluminum isopropoxide to 18.16 g of deionized water in a 125 mL plastic bottle and stirred at room temperature for 19 hours. After this 6.85 g orthophosphoric acid and 1.14 g of hydrochloric acid were added all at once to the mixture and the mixture was stirred for 75 minutes. Colloidal silica (2.00 g Ludox SM-30) was then added with stirring for 15 minutes. The mixture was then transferred to a Teflon liner and 28.12 g of 35% tetraethylammonium hydroxide were added and the mixture was stirred at room temperature for 22 hours. Crystallization was started in a stirred reactor at 215° C., then after 3.83 hours the reactor was cooled down to room temperature and the mixture inside was stirred for 6 days, then was transferred to a static autoclave for crystallization at 215° C. for 96 hours 40 minutes. Formed SAPO material was separated, washed with water, and dried at 90° C. overnight. Material was then sieved through a 40 mesh screen and calcined at 580° C. in air for 3 hours. This was designated as catalyst C.

Catalyst D.

A solution was prepared by adding 7.46 g of 85% orthophosphoric acid and 0.50 g of 37% hydrochloric acid to 18.16 g of deionized water with stirring. To this solution was then added 13.63 g of aluminum isopropoxide and 0.74 g of Ludox SM-30 colloidal silica with stirring. This mixture was stirred for 5 minutes, then 28.17 g of tetraethylammonium hydroxide were added to the mixture. This was then allowed to stir 16 hours at room temperature in a sealed Teflon liner. The mixture was then crystallized at 215° C. for 24 hours in a static reactor. Formed SAPO was separated, washed with water, then dried at 90° C. for 23 hours, then calcined by heating at 300° C. for 3 hours, then at 600° C. for 3 hours. This was designated as Catalyst D.

All catalysts were analyzed for Si, Al and P by XRF technique. The BET surface area (BET SA) and micropore area were measured by BET $N_2$ adsorption at −196° C. The results are shown Table 3.

TABLE 3

| Catalyst | XRF Elemental Analysis (wt. %) | | | | | $N_2$ Adsorption | |
|---|---|---|---|---|---|---|---|
| | % Si | % Al | % P | Si/$Al_2$ | Si/(Al + P) | BET SA, $m^2/g$ | Micro-Pore Area, $m^2/g$ |
| A | 6.77 | 23.86 | 15.63 | 0.55 | 0.17 | 546 | 525 |
| B | 6.44 | 23.35 | 17.80 | 0.53 | 0.16 | 454 | 426 |
| C | 3.52 | 22.85 | 19.97 | 0.26 | 0.08 | 487 | 467 |
| D | 1.42 | 23.84 | 19.37 | 0.11 | 0.03 | 504 | 483 |

Figure 3:
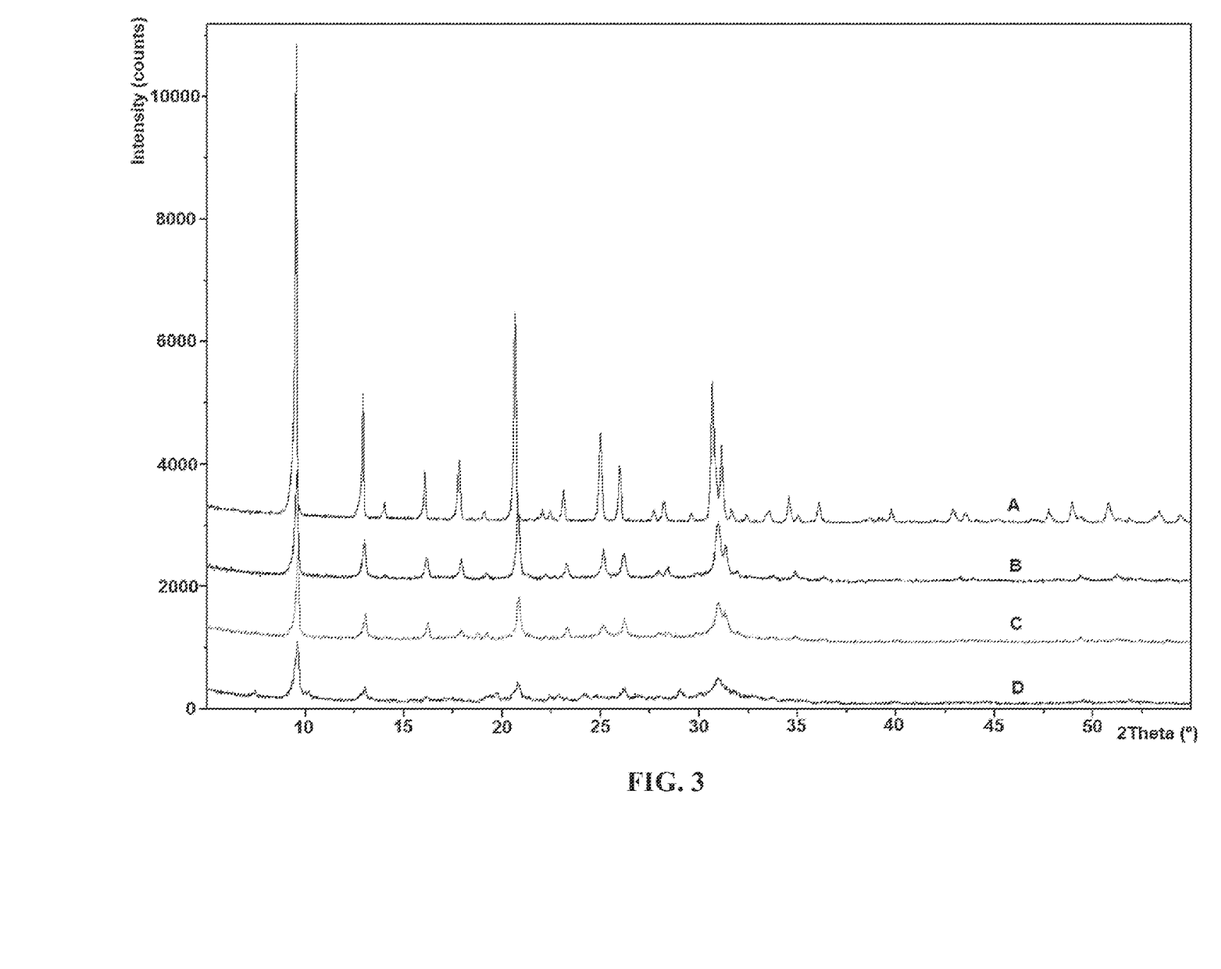
FIG. 3: X-ray powder diffraction patterns of Catalysts A, B, C and D (pattern A refers to Catalyst A, pattern B refers to Catalyst B, and so on).

X-ray powder diffraction patterns of the air-calcined SAPO-34 powder were recorded on a Philips PANanalytical X'Pert XRD System using CuKα radiation. FIG. 3 shows XRD patterns of Catalysts A, B, C and D. The characteristic peaks of SAPO-34 were observed at 2θ=9.5° and 20.6° for Catalysts A-D. In general, the XRD peak intensity was observed to decrease in the order of catalyst A>B>C>D where Si content decreases in the same order. Catalyst D shows a very weak peak at 2θ=5° assigned to SAPO-5.

Figure 4A:
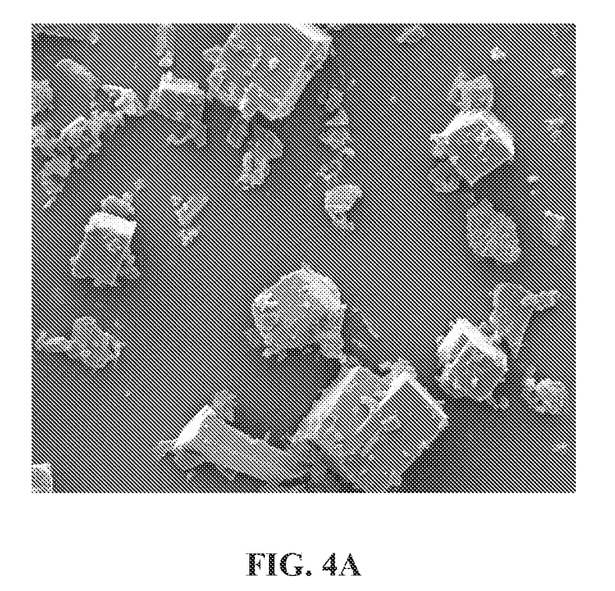
FIGS. 4A and 4B: SEM images of Catalyst A (FIG. 4A) and Catalyst D (FIG. 4B).
Figure 4B:
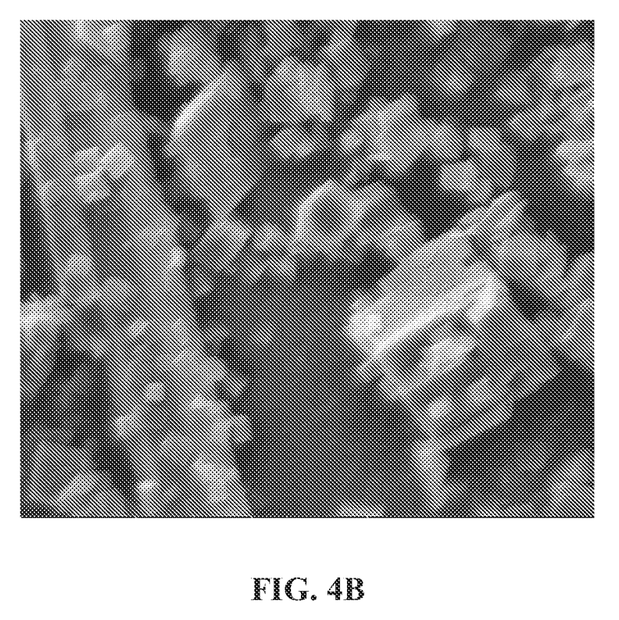

Scanning electron microscopy (SEM) images of the Catalysts A, B, C and D were recorded by JEOL 6400 instrument. Samples were sprinkled onto double stick carbon tape and were sputtered by using Au/Pd target at 10 mA for 30 minutes. 5-10 kV accelerating voltage beam was used for taking images. SEM images of Catalyst A (comparative catalyst) and Catalyst D (example catalyst) are shown in FIG. 4A and FIG. 4B, respectively. The SEM images showed cube shaped crystallites, typical for SAPO-34 formation. The particle size was analyzed by using Image-J software developed by NIST (National Institute of Standards and Technology). The images were processed with band-pass filter followed by assessing threshold each particle (amorphous materials were eliminated from the analysis) and finally particles were measured. The average particle size of the catalyst samples are shown in Table 4.

Figure 5:
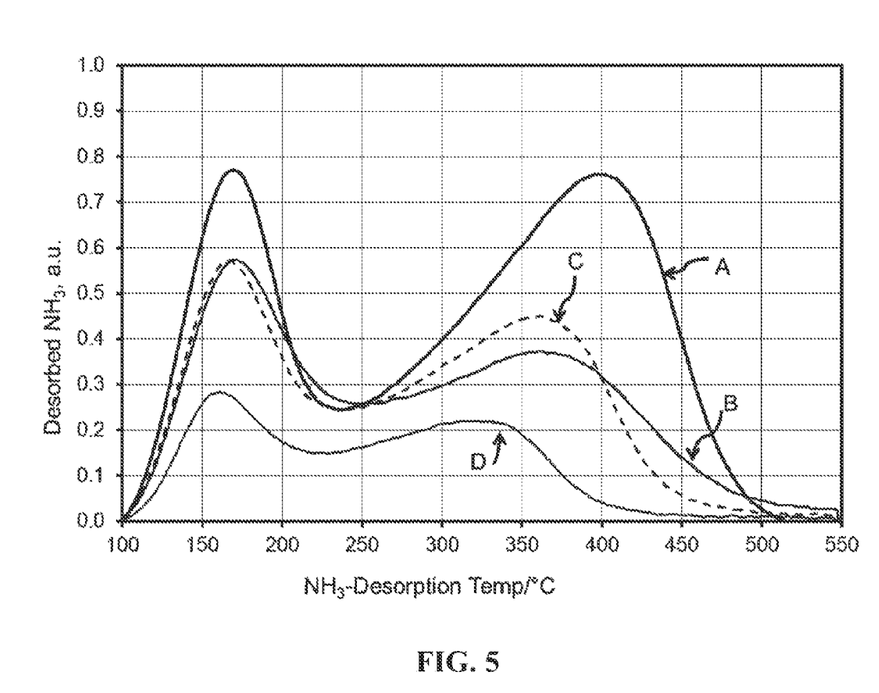
FIG. 5: $NH_3$-TPD of various SAPO-34 catalysts of the present invention (curve A refers to Catalyst A, curve B refers to Catalyst B, and so on).

FIG. 5 shows $NH_3$-TPD data for each of the Catalysts A-D. Catalyst A has $NH_3$-desorption peaks with maxima at around 165° C. and 395° C. attributing to weak and strong acid sites present in the catalyst. The acid concentrations were estimated from the area of the $NH_3$-desorption peaks. The acid concentrations of the catalysts are shown in Table 4. The catalysts produced in accordance with the present invention had peak size decreases and the maxima shift to lower temperature attributing to decrease of acid sites.

TABLE 4

| Catalyst | Acidity, mmol/g-cat | | | Avg. Particle Size (μm) |
|---|---|---|---|---|
| | weak | strong | total | |
| A | 0.55 | 1.47 | 2.01 | 1.46 |
| B | 0.50 | 0.75 | 1.26 | 0.24 |
| C | 0.43 | 0.78 | 1.21 | 0.55 |
| D | 0.20 | 0.37 | 0.57 | 0.41 |

Comparative Example 1 and Examples 2-4

In comparative example 1, Catalyst A was used for chloromethane conversion reaction, whereas in examples 2-4, Catalysts B, C and D were used for the same reaction. Each of the Catalysts A through D was tested for chloromethane conversion by using a fixed-bed tubular reactor at about 350° C. for a period of about 20 h or longer. For catalytic test the powder catalyst was pressed and then crushed and sized between 20 and 40 mesh screens. In each test a fresh load of sized (20-40 mesh) catalyst (3.0 g) was loaded in a stainless steel tubular (½-inch outer diameter) reactor. The catalyst was dried at 200° C. under $N_2$ flow (100 $cm^3$/min) for an hour and then temperature was raised to 300° C. at which time $N_2$ was replaced by methyl chloride feed (90 $cm^3$/min) containing 20 mol % $CH_3Cl$ in $N_2$. The weight hourly space velocity (WHSV) of $CH_3Cl$ was about 0.8 $h^{-1}$ to 1.0 $h^{-1}$ and reactor inlet pressure was about 1 to 3 psig. The reaction temperature was ramped to 350° C. after about 2-3 h of initial reaction period. Reaction conditions are summarized in Table 5. The pre- and post-run feeds were analyzed and the average was taken into calculations for catalyst performance.

TABLE 5

Reaction Conditions of Comparative Example 1 and Examples 2-4

| Example | Catalyst | Catalyst (g) | Feed Rate[1] (cm3/min) | WHSV ($h^{-1}$) | Temp (° C.) | Reactor Inlet Pressure (psig) |
|---|---|---|---|---|---|---|
| 1 (Comparative Example) | A | 3.01 | 90 | 0.9 | 349 | 2.5 |
| 2 | B | 3.01 | 90 | 1.0 | 350 | 1.5 |
| 3 | C | 3.01 | 90 | 0.9 | 348 | 3.3 |
| 4 | D | 3.00 | 90 | 0.8 | 350 | 1.8 |

[1]Total feed rate (feed contains 20 mol % $CH_3Cl$ in $N_2$)

Figure 6:
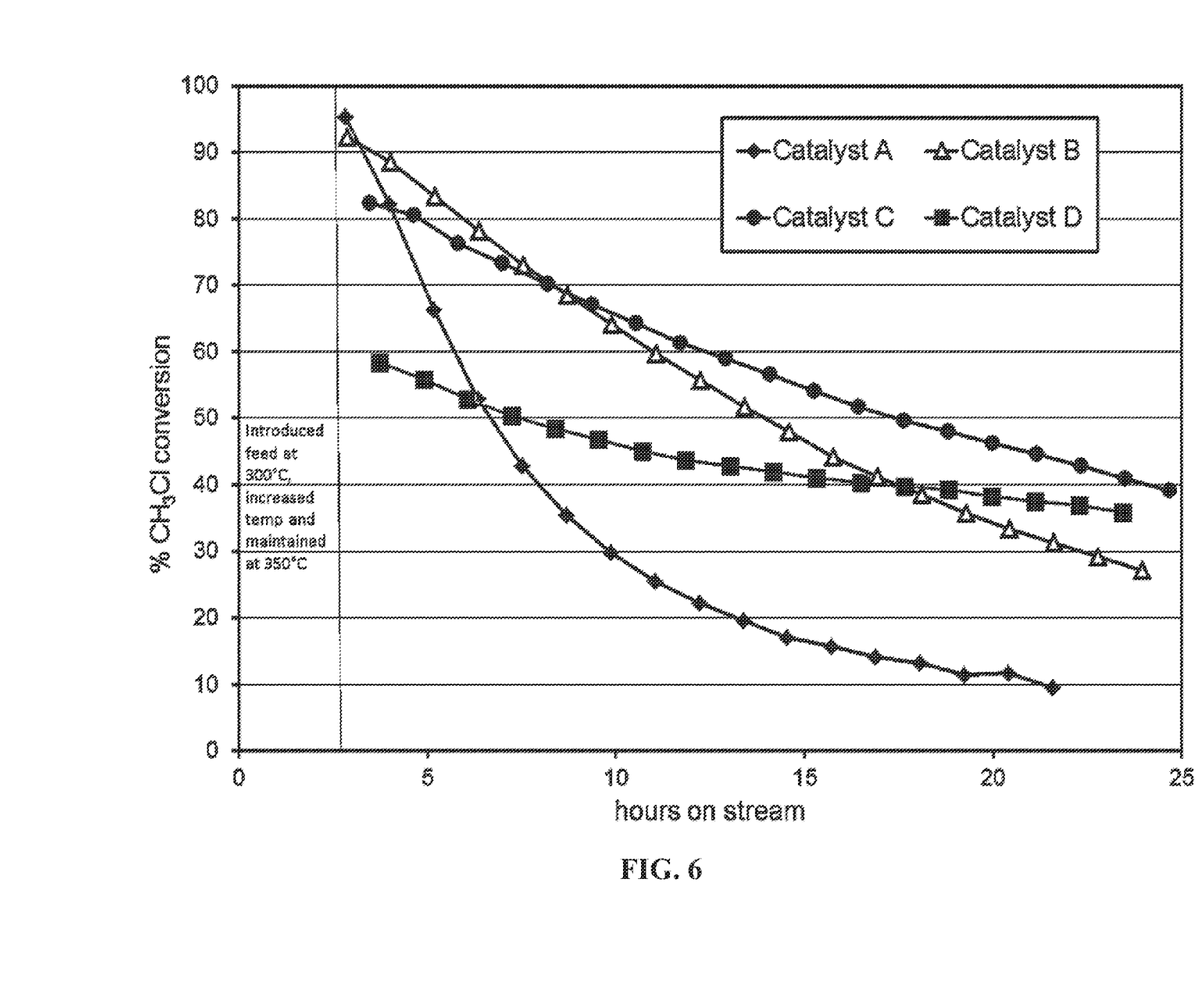
FIG. 6: $CH_3Cl$ conversion as a function of time on stream over SAPO-34 Catalysts A, B, C and D.

The conversion of chloromethane and selectivity of olefins were calculated using Equations 3-7 shown earlier. The conversion of chloromethane (after the induction time of about 3 h) at 3 h. In Table 6 also included are conversion and selectivities to ethylene, propylene and butylene at 20 h run time. FIG. 6 shows conversion of CH₃Cl over the sample catalysts. Catalysts A, B, C, and D show CH₃Cl conversion (at 3 h) of 91.1%, 91.5%, 83.2%, and 57.8%, respectively.

Figure 7:
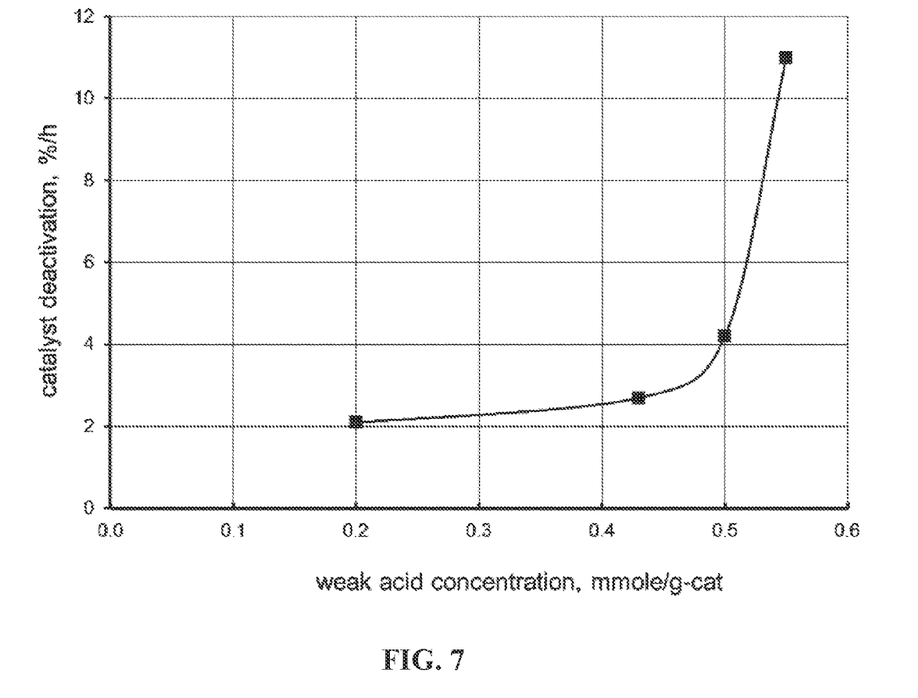
FIG. 7: Catalyst deactivation rate as a function of weak acid concentration.

Catalyst deactivation rate (% conversion decreased per hour) was calculated from the linear plot of conversion versus time-on-stream during 3-12 h (data obtained after the induction time of about 3 h) and the results are included in Table 6. FIG. 7 shows deactivation rate versus weak acid concentration. The catalyst deactivation rate was found to increase slowly with the increase of weak acid concentration up to catalyst containing about 0.5 mmol/g-cat (for Catalyst D, C and B) and increased rapidly for Catalyst A containing weak acid concentration of about 1.46 mmol/g-cat. The average particle size of Catalyst A is about 1.5 μm compared to 0.2 to 0.6 um for Catalyst B, C and D. The particle size may have contributed to rapid deactivation for Catalyst A as well.

In Table 6 summarized are chloromethane conversions at 3 h and 20 h, $C_2$-$C_4$ olefin selectivity at 20 h and catalyst deactivation data for the comparative Catalyst A and Catalysts B, C and D of the present invention. The deactivation rate of comparative Catalyst A (11% conversion decrease per hour) is greater than Catalysts B to D (2.1 to 4.2% conversion decrease per hour). The combined selectivity to $C_2$-$C_4$ olefins for comparative Catalyst A was about 88.5% whereas that for Catalysts B to D was about 95% or higher.

TABLE 6

| Catalyst | % Conversion | | Selectivity (% C-mol)[1] | | | Catalyst Deactivation[2] |
|---|---|---|---|---|---|---|
| | at 3 h | at 20 h | $C_2H_4$ | $C_3H_6$ | $C_4H_8$ | |
| A | 91.1 | 11.8 | 50.5 | 32.1 | 5.9 | 11.0 |
| B | 91.5 | 33.3 | 50.2 | 40.5 | 5.0 | 4.2 |
| C | 83.2 | 46.3 | 46.4 | 41.4 | 8.1 | 2.7 |
| D | 57.8 | 38.3 | 42.0 | 40.6 | 12.1 | 2.1 |

[1] Selectivity (% C-mol) at 20 h run time.
[2] Initial deactivation rate (% conversion decreased per hour) was calculated from linear plot of data obtained during about 3 h to 12 h run time.

Catalysts C and D, exhibited the most stability over prolonged periods of use. In particular, each of the catalysts having Si content less than 4 wt. %, weak acid concentration of less than 0.55 mmol/g-cat and total acid concentration of less than 1.26 mmol/g-cat had greater than 30% chloromethane conversion after 20 h time on stream at 350° C. Of particular note is the prolonged stability seen for Catalyst D, as its rate of deactivation from 15 to 20 hours substantially plateaus. By comparison, reference Catalyst A had less than 12% chloromethane conversion under the same reaction conditions. These data confirm the improved stability of the catalysts of the present invention.

The invention claimed is:

1. A method for converting an alkyl halide to an olefin, the method comprising contacting a silicoaluminophosphate (SAPO) catalyst with a feed comprising an alkyl halide under reaction conditions sufficient to produce an olefin hydrocarbon product comprising $C_2$ to $C_4$ olefins, wherein the SAPO catalyst has bimodal acidity designated as weak acid sites and strong acid sites, wherein the weak acid concentration is less than 0.55 mmol/g-cat and the total acid concentration is less than 1.5 mmol/g-cat.

2. The method of claim 1, wherein the SAPO catalyst has a weak acid concentration of 0.1 to 0.3 mmol/g-cat and a total acid concentration of less than 0.7 mmol/g-cat.

3. The method of claim 2, wherein the SAPO catalyst has 1 to 2 wt. % of Si.

4. The method of claim 1, wherein the SAPO catalyst has a weak acid concentration of 0.3 to 0.5 mmol/g-cat and a total a total acid concentration of 1.3 mmol/g-cat or less.

5. The method of claim 4, wherein the SAPO catalyst has 3 to 4 wt. % of Si.

6. The method of claim 1, wherein the SAPO catalyst is SAPO-34.

7. The method of claim 1, wherein the SAPO catalyst has an average particle size of 0.1 um to 1 μm.

8. The method of claim 1, wherein the SAPO catalyst has an average pore opening of 3.5 to 4.5 angstroms.

9. The method of claim 1, wherein the SAPO catalyst has a P content of 17 to 20 wt. % and an Al content of 22 to 24 wt. %.

10. The method of claim 9, wherein the SAPO catalyst has an Si/(Al+P) ratio of less than 0.17.

11. The method of claim 1, wherein the alkyl halide conversion is at least 25% at 20 hours of use at a temperature of 300° C. to 375° C. and a WHSV of the halide feed of 0.5 and 1.5 h⁻¹.

12. The method of claim 11, wherein the combined selectivity of ethylene and propylene is at least 80%.

13. The method of claim 1, wherein the SAPO catalyst has a weak acid concentration of 0.50 mmol/g-cat or less and a total acid concentration of 1.3 mmol/g-cat or less.

14. The method of claim 1, wherein the SAPO catalyst has 4 wt. % or less of Si.

15. The method of claim 1, wherein the SAPO catalyst deactivation rate is less than 5% alkyl halide conversion decrease per hour.

16. The method of claim 1, wherein the alkyl halide is a methyl halide, wherein the methyl halide is methyl chloride, methyl bromide, methyl fluoride, or methyl iodide, or any combination thereof.

17. The method of claim 1, wherein the feed comprises about 10 mol % or more of the alkyl halide.

18. The method of claim 1, further comprising regenerating the used catalyst after 20 hours of use.

19. The method of claim 1, wherein the SAPO catalyst has an average particle size of from 0.2 μm to 0.6 μm.

20. The method of claim 1, wherein the SAPO catalyst has an average particle size of about 0.4 μm.

* * * * *

UNITED STATES PATENT AND TRADEMARK OFFICE
CERTIFICATE OF CORRECTION

PATENT NO.        : 9,550,178 B2
APPLICATION NO.   : 14/907598
DATED             : January 24, 2017
INVENTOR(S)       : Ashim Kumar Ghosh et al.

It is certified that error appears in the above-identified patent and that said Letters Patent is hereby corrected as shown below:

In the Claims

In Claim 7 on Column 16, Line 20, "0.1 um" should read --0.1 μm--.

Signed and Sealed this
Twenty-first Day of March, 2017

Michelle K. Lee
*Director of the United States Patent and Trademark Office*